United States Patent [19]

Albright

[11] 4,049,617
[45] Sept. 20, 1977

[54] REACTIVE FLAME RETARDANTS

[75] Inventor: James A. Albright, Ann Arbor, Mich.

[73] Assignee: Velsicol Chemical Corporation, Chicago, Ill.

[21] Appl. No.: 650,172

[22] Filed: Jan. 19, 1976

[51] Int. Cl.² .................... C08K 5/51; C08K 5/52
[52] U.S. Cl. .................... 260/45.8 R; 260/2.5 AJ; 260/2.5 FP; 260/77.5 AR; 260/927 R; 260/937
[58] Field of Search .............. 260/45.8 R, 77.5 AR, 260/927 R, 937, 2.5 FP, 2.5 AJ

[56] References Cited

U.S. PATENT DOCUMENTS

| | | | |
|---|---|---|---|
| 3,046,236 | 7/1962 | Jahn | 260/2.5 FP |
| 3,385,801 | 5/1968 | Birum et al. | 260/2.5 AJ |
| 3,415,906 | 12/1968 | Shepard et al. | 260/937 |
| 3,459,835 | 8/1969 | Dever et al. | 260/927 R |
| 3,564,601 | 2/1971 | Witt et al. | 260/929 |
| 3,641,225 | 2/1972 | Dever et al. | 260/976 |
| 3,781,388 | 12/1973 | Jenkner et al. | 260/953 |
| 3,890,409 | 6/1975 | Mayerhoefer et al. | 260/927 R |
| 3,966,849 | 6/1976 | Noetzel et al. | 260/937 |
| 3,969,437 | 7/1976 | Shim | 260/937 |
| 4,012,466 | 3/1977 | Wang et al. | 260/937 |

*Primary Examiner*—Donald E. Czaja
*Assistant Examiner*—R. A. White
*Attorney, Agent, or Firm*—Robert M. Phipps

[57] ABSTRACT

Disclosed are novel compounds of the formula

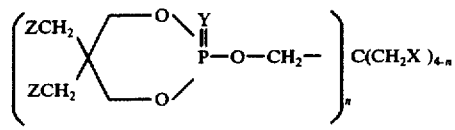

wherein each Z is independently selected from the group consisting of hydrogen and halogen; wherein each X is independently selected from the group consisting of hydrogen, halogen, and hydroxyl, provided that at least one X is hydroxyl; wherein Y is selected from the group comprising oxygen and sulfur; and wherein $n$ is an integer from 1 to 3. The above compounds are effective flame retardants in polyurethane and polystyrene polymeric compositions.

13 Claims, No Drawings

4,049,617

REACTIVE FLAME RETARDANTS

BACKGROUND OF THE INVENTION

1. Field of the Invention

Compounds which are phosphorus esters wherein such compounds contain one to three 1,3,2-dioxophosphorinane rings. The compounds within the scope of this invention are also flame retardants for polyurethane and polystyrene polymeric compositions.

2. Description of the Prior Art

During the past several years, a large number of flame retardants have been developed for use with an almost equally large number of flammable materials. Cellulosic materials such as paper and wood and polymeric materials such as polyolefins, polyurethane, and polystyrene are just two examples of materials for which flame retardants have been developed. For any class of flammable materials, such as synthetic type polymers, those skilled in the art have long been aware that some flame retardant additives are more effective in polymers and polymeric compositions than other flame retardant additives. This is because the efficacy of any flame retardant in polymers or polymeric compositions is measured not only by the flame retardant capability of the additive but also by the ability of the additive to improve or modify, or at least not to detract from, other physical or mechanical properties of the polymer or polymeric composition. The mere fact, therefore, that most flame retardants contain halogen and phosphorus atoms does not assure that any given halogenated or phosphorus-containing compound will impart usable flame retarding charcteristics to all or even to any polymeric system. Furthermore, as those skilled in the art have improved the flame retardancy of many polymeric materials, they have been simultaneously required to provide the necessary flame retardancy with a minimal effect upon other properties of the polymer such as the light stability, processability, and flexural, tensile and impact strengths. Also, it has been the desire of those involved in the art of flame retardants to provide flame retardants having a durable lasting effect. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

In particular, U.S. Pat. No. 3,784,592 discloses that three moles of dibromoneopentyl glycol can be reacted with one mole of phosphorus oxychloride to produce tris(2,2-bis(bromomethyl)-3-propanol)phosphate, a compound having a structure very different from the novel reactive flame retardant compounds of this invention.

U.S. Pat. No. 2,952,701 (hereinafter referred to as McConnell et al.) discloses, inter alia, compounds of the formula:

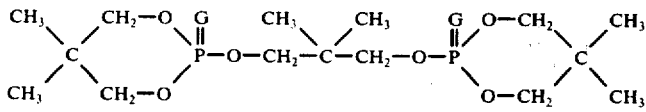

wherein G is selected from the group consisting of oxygen and sulfur. The organophosphorus compounds within the scope of McConnell et al. are useful as flameproofing plasticizers, stabilizers, synthetic lubricants, force transmission fluids, lubricating oil additives, pesticides, and intermediates for the preparation of other organophosphorus compounds.

U.S. Pat. No. 3,890,409 (hereinafter referred to as Mayerhoefer et al.) disclose compounds of the formula:

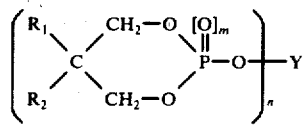

wherein $R_1$ and $R_2$ are each, independently, hydrogen or alkyl of 1 to 5 carbon atoms, and $n$, inter alia, may be 1 and Y can be, inter alia, $$-CH_2-C(CH_2X)_2$$
$$\phantom{-CH_2-C(}Z$$

wherein each X is, independently, chlorine or bromine and Z is alkyl of 1 to 4 carbon atoms or

wherein X is as defined above, and m is zero or the integer 1. Mayerhoefer et al. disclose that their compounds are useful flame retardants.

German 2,262,336 (hereinafter referred to as Shim) discloses flame retardant halogenated neopentylglycolmonophosphate and diphosphate esters of the formulas:

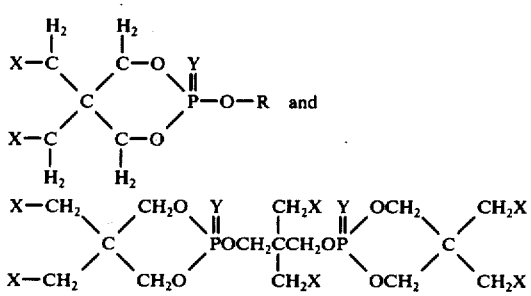

wherein R represents, inter alia, $C_1$ to $C_{10}$ alkyl-, a $C_1$ to $C_{10}$ halogenalkyl-, and a $C_1$ to $C_{10}$ hydroxyalkyl-. X represents halogen such as preferably bromine, while R is preferably, inter alia, a $C_1$ to $C_4$ haloalkyl-. Y is either oxygen or sulfur, preferably oxygen.

Neither McConnell et al. nor Mayerhoefer et al. nor Shim disclose that their respective compounds can contain methylol substitutes attached to the 2' carbon atom. As those skilled in the art of flame retardants know, the indiscriminate substitution of a hydroxyl group for a halogen or hydrogen atom of a compound will result in a dramatic decrease in the modified hydroxy substituted compound's hydrolytic and thermal stability. However, by the use of a high degree of inventive skill, it is possible to effectuate a substitution of a hydroxyl group for a halogen or hydrogen atom and still maintain the basic physical properties of the nonhydroxyl-containing compound. The net result of this inventive skill is that one is thereby able to produce a reactive flame retardant capable of reactively being bound into a polymer chain, e.g., polyurethane and polyester, and thereby reducing the migration of the flame retardant and the subsequent flame retardancy loss of the polymeric composition. This result has long been sought after and much desired in the art of flame retardants.

SUMMARY OF THE INVENTION

A compound of the formula

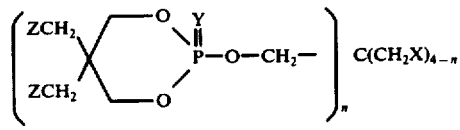
(I)

wherein each Z is independently selected from a group consisting of hydrogen and halogen; wherein each X is independently selected from a group consisting of hydrogen, halogen, and hydroxyl, provided that at least one X is hydroxyl; wherein Y is selected from the group comprising oxygen and sulfur; and wherein n is an integer from 1 to 3. Also within the scope of this invention is a polymeric composition comprising a polymer selected from the group consisting of polyurethane and polystyrene and a flame retarding amount of the above described compound.

DESCRIPTION OF THE PREFERRED EMBODIMENTS

The flame retardant compounds within the scope of this invention have the formula I above wherein each Z is independently selected from a group consisting of hydrogen and halogen, preferably halogen, and more preferably chlorine and bromine; wherein each X is independently selected from a group consisting of hydrogen, halogen, and hydroxyl, preferably halogen and hydroxyl, and more preferably chlorine, bromine, and hydroxyl, provided that at least one X is hydroxyl; wherein Y is selected from the group comprising oxygen and sulfur, preferably oxygen; and where n is an integer from 1 to 3, preferably from 1 to 2, and more preferably 1. For purposes of illustration only, Table I as follows is designed to further help describe the compounds within the scope of formula I.

The numerical designation used in naming the compounds within the scope of this invention can be ascertained by reference to the following formula wherein the members of the heterocyclic ring as well as the members of the bridging group are numbered.

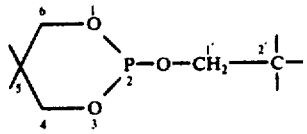

Three representative compounds are: 2-(2',2'-bis(-bromomethyl)-3'-hydroxypropoxy)-5,5-bis(bromomethyl)-2-oxo-1,3,2-dioxophosphorinane; 2',2'-bis(hydroxymethyl)-1', 3'-bis(5,5-bis(bromomethyl)-2-oxo-1,3,2-dioxophosphorinane)propane; and 2'-hydroxymethyl-1',3'-bis(5,5-bis-(bromomethyl)-2-oxo-1,3,2-dioxophosphorinane)-2'-(5,5-bis(bromomethyl)-2-oxo-1,3,2-dioxophosphorinane-2-methoxy)propane.

The following is a partial listing of the preferred compounds within the scope of this invention: 2-(2',2'-bis(-bromomethyl)-3'-hydroxypropoxy)-5,5-bis(bromomethyl)-2-oxo-1,3,2-dioxophosphorinane; 2-(2',2'-bis(-chloromethyl)-3'-hydroxypropoxy)-5,5-bis(chloromethyl)-2-oxo-1,3,2-dioxophosphorinane; 2-(-2',2'-bis(hydroxymethyl)-3'-bromopropoxy)-5,5-bis(bromomethyl)-2-oxo-1,3,2,-dioxophosphorinane; 2-(2',2'-bis(hydroxymethyl)-3'-chloropropoxy)-5,5-bis(chloromethyl)-2-oxo-1,3,2,-dioxophosphorinane; 2',2'-bis(hydroxymethyl)-1',3'-bis(5,5-bis(bromomethyl)-2-oxo-1,3,2-dioxophosphorinane)-propane; and 2',2'-bis(hydroxymethyl)-1',3'-bis(5,5-bis(chloromethyl)-2-oxo-1,3,2-oxophosphorinane)propane.

The compounds within the scope of this invention are prepared according to the general reaction scheme:

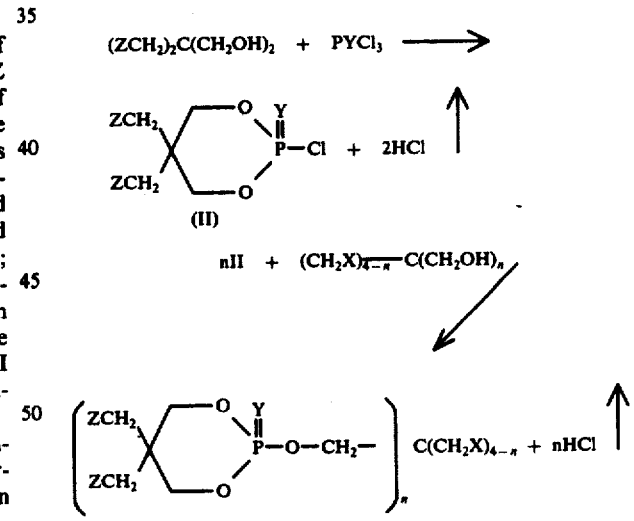

TABLE I

| Compound | n | X | X | X | Y | Y | Y | Z | Z | Z | Z | Z |
|---|---|---|---|---|---|---|---|---|---|---|---|---|
| 1 | 1 | Br | Br | OH | O | — | — | Br | Br | — | — | — |
| 2 | 1 | Cl | Cl | OH | O | — | — | Cl | Cl | — | — | — |
| 3 | 1 | Br | OH | OH | O | — | — | Br | Br | — | — | — |
| 4 | 1 | Cl | OH | OH | O | — | — | Cl | Cl | — | — | — |
| 5 | 2 | OH | OH | — | O | O | — | Br | Br | Br | Br | — |
| 6 | 2 | OH | OH | — | O | O | — | Cl | Cl | Cl | Cl | — |
| 7 | 3 | OH | — | — | O | O | O | Br | Br | Br | Br | Br |
| 8 | 3 | OH | — | — | O | O | O | Cl | Cl | Cl | Cl | Cl |
| 9 | 2 | OH | Br | — | O | O | — | Br | Br | Cl | Cl | — |
| 10 | 2 | OH | Cl | — | O | O | — | Br | Br | Cl | Cl | — |
| 11 | 2 | OH | OH | — | O | O | — | Br | Br | Cl | Cl | — |
| 12 | 3 | OH | — | — | O | O | O | Br | Br | Br | Cl | Cl |
| 13 | 3 | OH | — | — | O | O | O | Br | Br | Cl | Cl | Cl |
| 14 | 1 | OH | OH | OH | O | — | — | Br | Br | — | — | — |

TABLE I-continued

| Compound | n | X | X | X | Y | Y | Y | Z | Z | Z | Z | Z | Z |
|---|---|---|---|---|---|---|---|---|---|---|---|---|---|
| 15 | 1 | OH | OH | OH | O | — | — | Cl | Cl | — | — | — | — |
| 16 | 1 | Br | Cl | OH | O | — | — | Br | Br | — | — | — | — |
| 17 | 1 | Br | Cl | OH | O | — | — | Cl | Cl | — | — | — | — |
| 18 | 2 | OH | Br | — | O | O | — | Br | Br | Br | Br | — | — |
| 19 | 2 | OH | Cl | — | O | O | — | Cl | Cl | Cl | Cl | — | — |
| 20 | 2 | OH | Cl | — | O | O | — | Br | Br | Br | Br | — | — |
| 21 | 1 | Br | Br | OH | S | — | — | Br | Br | — | — | — | — |
| 22 | 1 | Cl | Cl | OH | S | — | — | Cl | Cl | — | — | — | — |
| 23 | 2 | OH | OH | — | S | S | — | Br | Br | Br | Br | — | — |
| 24 | 2 | OH | OH | — | S | S | — | Cl | Cl | Cl | Cl | — | — |
| 25 | 3 | OH | — | — | S | S | S | Br | Br | Br | Br | Br | Br |
| 26 | 1 | OH | H | H | O | — | — | H | H | — | — | — | — |
| 27 | 1 | OH | Br | Br | O | — | — | H | H | — | — | — | — |
| 28 | 1 | OH | H | H | O | — | — | Br | Br | — | — | — | — |
| 29 | 1 | OH | H | H | S | — | — | H | H | — | — | — | — |
| 30 | 3 | OH | — | — | O | O | O | H | H | H | H | H | H | wherein n, X, Y, and Z, have been defined above. In general, equal molar amounts of dihaloneopentyl glycols and phosphorous oxychloride or phosphorous thiochloride are reacted at a temperature from about 0° to about 120° C. until the theoretical amount of hydrogen chloride is evolved. The reaction can be carried out in the presence or absence of a solvent. Exemplary solvents include benzene, toluene, and chloroform. Catalytic quantities of a metal salt or oxide such as magnesium oxide, magnesium chloride, calcium oxide, calcium chloride, titanium chloride, or vanadium acetate, or stochiometric quantities of a weak organic base acid acceptor such as pyridine or triethylamine, can be used to accelerate the completion of the reaction. The crude product, 5,5-bis(halomethyl)-2-oxa-2-chloro-1,3,2-dioxophosphorinane is then treated with the desired stochiometric ratio of the desired polyol, e.g., pentaerythritol, dibromoneopentyl glycol, monochloropentaerythritol, etc., using the same reaction environment and conditions as in the initial reaction between the dihaloneopentyl glycol and phosphorous oxychloride or thiochloride, i.e., a reaction temperature of from about 0° to about 120° C., the presence or absence of a solvent, and the presence or absence of a metal catalyst or tertiary amine base, until the theoretical amount of hydrogen chloride is evolved.

Depending upon the physical condition of the final end product, various post-reaction treatments can be used. In the case of a liquid final product, said liquid product is washed with aqueous ammonia to remove any residual acidity. The aqueous ammonia wash is followed by a water wash. The washed product is dried by standard techniques, e.g., at a temperature of from about 100° to about 130° C. until constant weight is achieved.

When a solid product is obtained, said solid product can be purified by washing or recrystallization by techniques which are well known to those skilled in the art, e.g., the solid product can be washed with water or organic solvents such as benzene, toluene, methanol, ethanol, etc., or recrystallized from said solvent. The purified solid product is then dried by standard techniques, e.g., at a temperature of from about 50° to about 150° C. until constant weight is achieved.

Compounds of the present invention are useful as flame retardants in polymeric compositions. Polymers applicable to the present invention consist of polyurethanes, including flexible and rigid foams and elastomers, and styrene polymers such as polystyrene, including both crystalline and high impact types, and styrene co- and terpolymers such as styrene-acrylonitrile copolymer, styrene-butadiene copolymer, and acrylonitrile-butadiene-styrene terpolymers. A further description of above polymers applicable to the present invention may be found in Modern Plastics Encyclopedia, Vol. 52, No. 10A, McGraw-Hill, Inc., New York, New York (1975), said publication being incorporated herein in toto by reference.

Because the flame retardants within the scope of this invention contain an hydroxyl radical, said flame retardants should be particularly desirable in polymeric systems wherein they are capable of reacting into the polymer chain and thereby imparting a durable flame retarded polymeric composition. Among the polymer systems wherein the reactive hydroxyl group may bind into the polymer chain include polyesters, both saturated and unsaturated polyesters, polyurethanes, including flexible and rigid foams and elastomers, cellulosic polymers, e.g., cotton, and cellulosic-polyester blends, e.g., 50/50, 65/35, and 35/65 cotton/polyester blends, and epoxies.

The flame retardants within the scope of this invention may be incorporated into or applied onto the above polymers by techniques which are standard or known to those skilled in the art. See, for example, J. M. Lyons, "The Chemistry and Use of Fire Retardants", Wiley-Inter-science, New York, 1970, and Z. E. Jolles, "Bromine and its Compounds", Academic Press, New York, 1966.

The amount of flame retardant which is used in the compositions and in the methods of this invention is that amount necessary to produce measurable flame retardancy in the compositions which are so modified. Depending upon the particular compound and the particular polymer with which it is combined, the quantity of flame retardant employed in the compositions and methods of this invention can be of any amount up to about 35 percent or more by weight of the total composition. For most compositions, a flame retardant will comprise from about 1 to about 25 percent by weight of the total composition.

In addition to the flame retardant compounds within the scope of this invention, the flame retardancy of a polymer can be further enhanced through the use of so-called "synergists" or enhancing agents which, when used with the compounds of formula I, promote a cooperative effect therebetween and thus enhance the flame retardancy of the resultant plastic composition as compared to the flame retardancy of either one component used separately. These "enhancing agents" comprise the oxides and halides of groups IVA and VA of the Periodic Table, i.e., oxides and halides of antimony, bismuth, arsenic, tin, lead, germanium, e.g., antimony oxychloride, antimony chloride, antimony oxide, stannic oxide, stannic chloride, arsenous oxide, arsenous chloride, and the like; and organic and inorganic compounds of phosphorus, nitrogen, boron, and sulfur, e.g., triphenyl phosphate, ammonium phosphate, zinc borate, thiourea, urea, stannic sulfide, and the like and oxides and halides of titanium, vanadium, chromium, manganese, iron, niobium, molybdenum, copper, zinc, magnesium, e.g., titanium dioxide, titanium chloride, vanadium pentoxide, chromic bromide, manganous oxide, molybdenum trioxide, ammonium molybdate; and hydrates of the above, e.g., stannous oxide hydrate, lead hydrate; and combinations thereof. The preferred enhancing agents are the oxides of antimony, arsenic and bismuth. However, any compound which on decomposition, as by ignition, yields these oxides would be suitable. Thus some organic antimonates are preferred. The enhancing agents disclosed in U.S. Pat. No. 3,205,196 are also suitable for use.

U.S. Pat. No. 3,205,196, column 2, states that "Antimony oxide" is the antimony compound that is presently preferred for use in the present invention. However, many antimony compounds are suitable, inorganic antimony compounds include antimony sulfide, sodium antimonite, potassium antimonite, and the like. Many organic antimony compounds are suitable such as the antimony salts of organic acids and their pentavalent derivatives disclosed in copending application Ser. No. 688,143, filed Oct. 4, 1957, now U.S. Pat. No. 2,996,528. Compounds of this class include antimony butyrate, antimony valerate, antimony caproate, antimony heptylate, antimony caprylate, antimony pelargonate, antimony caprate, antimony cinnamate, antimony anisate, and their pentavalent dihalide derivatives. Likewise the esters of antimonous acids and their pentavalent derivatives disclosed in copending application Ser. No. 688,108, filed Oct. 4, 1957, now U.S. Pat. No. 2,993,924, such as tris(n-octyl) antimonite, tris(2-ethylhexyl) antimonite, tribenzyl antimonite, tris($\beta$-chloroethyl) antimonite, tris($\beta$-chloropropyl) antimonite, tris($\beta$-chlorobutyl) antimonite and their pentavalent compounds are the cyclic antimonites such as trimethylolpropane antimonite, pentaerythritol antimonite, and glycerol antimonite. The corresponding arsenic and bismuth compounds can also be employed."

It is to be understood that such patents as U.S. Pat. No. 3,205,196; 2,996,528 and 2,993,924 are to be considered as incorporated herein by reference for all intents and purposes. Without limitation, preferred enhancing agents include $Sb_2O_3$, $SbCl_3$, $SbBr_3$, $SbI_3$, $SbOCl$, $As_2O_3$, $As_2O_5$, $ZnBO_4$, $BaB_2O_4 \cdot H_2O$, $2 \cdot ZnO \cdot 3B_2O_3 \cdot 3 \cdot 5H_2O$ and stannous oxide hydrate. The more preferred enhancing agent is antimony trioxide.

It is also within the scope of the present invention to employ other materials in the present invention compositions where one so desires to achieve a particular end result. Such materials include, without limitation, adhesion promotors; antioxidants; antistatic agents; antimicrobials; colorants; flame retardants such as those listed on pages 665 to 668, Modern Plastics Encyclopedia, ibid., (in addition to the new class of flame retardants described herein); heat stabilizers; light stabilizers and fillers.

In this latter category, i.e., fillers, there can be mentioned without limitation, materials such as glass; carbon; cellulosic fillers (wood flour, cork and shell flour); calcium carbonate (chalk, limestone, and precipitated calcium carbonate); metal flakes; metallic oxides (aluminum, beryllium oxide and magnesia); metallic powders (aluminum, bronze, lead, stainless steel and zinc); polymers (comminuted polymers and elastomerplastic blends); silica products (diatomaceous earth, novaculite, quartz, sand, tripoli, fumed colloidal silica, silica aerogel, wet process silica); silicates (asbestox, kaolimite, mica, nepheline syenite, talc, wollastonite, aluminum silicate and calcium silicate); and inorganic compounds such as barium ferrite, barium sulfate, molybdenum disulfide and silicon carbide.

The above mentioned materials, including filler, are more fully described in Modern Plastics Encyclopedia, ibid., and which publication has been incorporated herein in toto by reference.

The amount of the above described materials employed in the present invention compositions can be any quantity which will not substantially adversely affect the desired results derived from the present invention compositions. Thus, the amount used can be zero (0) percent, based on the total weight of the composition, up to that percent at which the composition can still be classified as a plastic. In general, such amount will be from about 0% to about 75% and more specifically from about 1% to about 50%.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

Preparation of compound 1 of Table I:

A five-liter flask, equipped with a condenser, stirrer, and thermometer, was charged with 1048 grams of dibromoneopentyl glycol, 614 grams of phosphoryl chloride and 3 grams of magnesium oxide. The mixture was stirred and heated to 60° C. and held at that temperature for two hours. The temperature was slowly raised to 85° C. and held at 85° C. for three hours, and then 995 grams of dibromoneopentyl glycol were added. The mixture was heated to 100° C. and held for three hours. After cooling to 60° C., 1600 ml. of methanol was added. A white solid separated and 500 ml. of water was added. After filtering and drying, 1602 grams of a white solid having a melting point of from 119° to 122° C. resulted. This material was identified by NMR analysis and found to have a purity of greater than 95 percent.

EXAMPLE 2

Preparation of compound 3 of Table I:

Dibromoneopentyl glycol (164.5 grams), 0.3 grams of magnesium oxide, and 96.3 grams of phosphorus oxychloride were heated to 100° C. in a 500-ml. flask equipped with a condenser, stirrer, and thermometer. The temperature was raised to 100° C. over a one-half hour period and held at 200° C. for two hours. An aspirator was connected for one-half hour at 100° C. The reacted product was cooled to room temperature under an aspirator vacuum. Monobromopentaerythritol (125 grams) was added. The resulting mixture was heated to 100° to 105° C. After one-half hour at 100° C. an aspirator was connected and the reaction was maintained at 100° C. under an aspirator vacuum for an additional five and three-quarter hours. Later, the reaction product was cooled to 50° C. and washed with an aqueous ammonia solution. The product was cooled to room temperature, washed with water at 50° C., dissolved in acetone and dried. The yield was 143 grams (45 percent). Percent bromine calculated: 47.5; percent bromine found: 50.52. Hydroxyl number calculated: 222; hydroxyl number found: 175. Acid number: none detected.

In a similar manner other flame retardants within the scope of this invention, e.g., 2-(2',2'-bis(chloromethyl)-3'-hydroxypropoxy)-5,5-bis(chloromethyl)-2-oxo-1,3,2-dioxophosphorinane, 2-(2',2'-bis-(hydroxymethyl)-3'-chloropropoxy)-5,5-bis(chloromethyl)-2-oxo-1,3,2-dioxophosphorinane, 2',2'-bis(hydroxymethyl)-1',3'-bis(5,5-bis(bromomethyl)-2-oxo-1,3,2-dioxophosphorinane)propane, and 2',2'-bis-(hydroxymethyl)-1',3'-bis(5,5-bis(chloromethyl)-2-oxo-1,3,2-dioxophosphorinane)propane, can be prepared.

EXAMPLE 3

A foam was prepared using the following basic formulation:

| Component | Parts by Weight |
|---|---|
| Polyol[a] | 100 |
| Silicone Glycol Surfactant[b] | 2 |
| Trichlorofluoromethane[c] | 35 |
| Polyisocyanate[d] | 135 |

[a]alkanolamine polyol, molecular weight approximately 3500, hydroxyl number approximately 530, Thanol R-350-X, brand polyol, Jefferson Chemical Co., Houston, TX.
[b]Dow Corning 193 brand surfactant, Dow Corning Corp., Midland, MI.
[c]Freon 11B brand trichlorofluoromethane, E. I. Du Pont de Nemours & Co., Wilmington, DE.
[d]Polymeric aromatic isocyanate, 31.5% available NCO, Mondur MRS brand polyisocyanate, Mobay Chemical Co., Pittsburgh, PA.

The polyol, surfactant, and flurocarbon blowing agent were combined in a masterbatch based on 1000 gm of polyol to minimize loss of blowing agent.

The following procedure was used to prepare the foam:

1. The polyisocyanate was weighed into a tared, 10-ounce, paper cup (allowances being made for hold-up) and the cup set aside while the remaining ingredients were weighed out and mixed.
2. The polyol masterbatch was weighed out, in the proper amount to give 100 grams of polyol, in a one quart, untreated, paper cup.
3. The 10 grams of 2-(2',2'-bis(hydroxymethyl)-3-bromopropyl)-5,5-bis(bromomethyl)-2-oxo-1,3,2-dioxophosphorinane were then weighed into the same one quart cup.
4. The contents of the one quart cup were mixed at 1000 rpm for 5 seconds.
5. The polyisocyanate was then added and stirring at 1000 rpm continued for 10 seconds.
6. The mix was poured into a 5-pound, untreated, paper tub and allowed to rise.

After the foam was tack-free and substantially cured, it was set aside for at least seven days prior to subjecting said foam to an Oxygen Index Test, ASTM D-2863-74. The results of said test are reported in Table II.

The same procedure was used to make other foams at different load levels and sometimes also containing a different flame retardant additive. These foams were also subjected to the same Oxygen Index Test as the above foam and the data are also reported in Table II.

TABLE II

| Flame Retardant | Load Level, php[a] | OI, percent |
|---|---|---|
| Control | 0 | 21.0 |
| (Table I, compound 3) | 10 | 23.5 |
|  | 20 | 24.5 |
| (Table I, | 30 | 24.0 |

TABLE II-continued

| Flame Retardant | Load Level, php[a] | OI, percent |
|---|---|---|
| compound 1) | | |

[a]php means parts per hundred polyol.

EXAMPLE 4

An 80/20 mixture of toluene 2,4- and 2,6-diisocyanate, Type I, (hereinafter referred to as TDI) was placed in the first tank of a Martin Sweets Modern Module No. 3A urethane foam equipment modified for simultaneous addition of up to six components. The flame retardant of Table I, compound 3 (0.5 kg) was mixed with 10 kg of polyol in a second tank (Pluracol GP 3030 brand polyol BASF Wyandotte, Wyandotte, MI., is a polypropylene glycol having a molecular weight of approximately 3000 and a hydroxyl number of approximately 56.). Stannous octoate catalyst was placed in a third tank (T-9 brand catalyst, M & T Chemicals, Inc., New York, New York). Into a fourth tank was placed a silicone surfactant (L-540 brand surfactant, Union Carbide Corp., New York, New York). Water/triethylene diamine (Dabco 33LV brand) mixture 3.0/(0.20 to 0.40) was added to a fifth tank. (Dabco 33LV, Houndry Process & Chemical Co. is a 33% solution of triethylene diamine in dipropylene glycol.) All of the above components were pumped at a predetermined rate simultaneously into a chamber and were mixed using a size 3 pin type mixer revolving at 3,000 rpm in the following ratio:

| Component | Parts by Weight |
|---|---|
| Flame retardant of Table I, compound 3 | 5 |
| Polyol | 100 |
| Silicone surfactant | 1.0 to 1.5 |
| Triethylene diamine | 0.40 to 0.42 |
| Stannous octoate catalyst | 0.10 to 0.18 |
| Water | 3.0 |
| TDI | 103 to 105 index |

The mixture was dropped during the mixing procedure into a 14 inch × 14 inch × 6 inch Adstrom cardboard box. After the foam came to full height it was post cured in a forced air oven at 210° to 220° F. for 30 minutes.

After allowing the foam to sit for at least seven days, the foam was then subjected to the several tests listed in Table III.

The same procedure was used to make other foams at different load levels. These foams were also subjected to the same tests as the above foam and the data obtained is also reported in Table III.

TABLE III

Combustibility of Molded Urethane Foams

| Flame Retardant Load Level | Control | 5 php | 10 php |
|---|---|---|---|
| MVSS302, in/min[a] | | | |
| Initial | pass, 3.98 | pass, 0 | pass, 0 |
| Aged[b] | N.D.[d] | pass, 0 | pass, 0 |
| Aged[c] | pass, 3.5 | pass, 0 | pass, 0 |

[a]MVSS302 is the Motor Vehicle Safety Standard 302, Department of Transportation.
[b]Aged as per ASTM-D-1564, dry heat 140° C., 22 hours.
[c]Aged as per FBMS TM 10-12, General Motors Corporation.
[d]N.D. means not determined.

EXAMPLE 5

A solution of 600 grams of polystyrene and 2.5 parts per hundred resin (phr) of the flame retardant of Table I, compound 1 in 270 grams of methylene chloride and 60 grams of hexane was prepared. To the above solution was added 3 grams of dicumyl peroxide as a flame retardant synergist. This mixture was poured into a polyethylene dish and the methylene chloride was allowed to evaporte in the air. Following this, the casting was steamed to produce a crude foam. This foam was then cut into sufficient specimens of appropriate sizes in order to subject said foam to various tests and the data obtained therefrom are reported in Table IV.

Additional samples of polymer were prepared having different flame retardant load levels. These samples were tested in the same manner and the results obtained are also tabulated in Table IV.

TABLE IV

| Flame Retardant | Load Level, phr | OI,[1] percent |
| --- | --- | --- |
| Control | 0 | 19.5 |
| Table I, | 2.5 | 23.5 |
| compound 1 | 5.0 | 25.5 |

[1] ASTM D-2863-74

As Tables III and IV clearly indicate, the compounds within the scope of thie invention, as exemplified by 2-(2',2'-bis(hydroxymethyl)-3'-bromopropoxy)-5,5-bis(-bromomethyl)-2-oxo-1,3,2-dioxophosphorinane and 2-(2',2'-bis(bromomethyl)-3'-hydroxypropoxy)-5,5-bis(-bromomethyl)-2-oxo-1,3,2-dioxophosphorinane, respectively, possess excellent flame retardant efficacy in polyurethanes, as exemplified by molded urethane foam, and styrene polymers as exemplified by crystalline foam polystyrene. Exemplary flame retardants within the scope of formula I which also display excellent flame retardant efficacy in polyurethanes and polystyrene include 2-(2',2'-bis-(chloromethyl)-3'-hydroxypropoxy)-5,5-bis(chloromethyl)-2-oxo-1,3,2-dioxophosphorinane, 2-(2',2'-bis(hydroxymethyl)-3'-chloropropoxy)-5,5-bis(chloromethyl)-2-oxo-1,3,2-dioxophosphorinane, 2',2'-bis(hydroxymethyl)-1',3'-bis(5,5-bis(-bromomethyl)-2-oxo-1,3,2-dioxophosphorinane)propane and 2',2'-bis(hydroxymethyl)-1',3'-bis(5,5-bis(-chloromethyl)-2-oxo-1,3,2-dioxophosphorinane)propane. The compounds 2-(2',2'-bis(bromomethyl)-3'-hydroxypropoxy)-5,5-bis-(bromomethyl)-2-oxo-1,3,2-dioxophosphorinane and 2-(2',2'-bis-(hydroxymethyl)-3'-bromopropoxy)-5,5-bis(bromomethyl)-2-oxo-1,3,2-dioxophosphorinane also display excellent flame retardant efficacy in polyurethanes and styrene polymers respectively.

EXAMPLE 6

In order to demonstrate that the indiscriminate substitution of an hydroxyl group for a halogen substituent of a particular compound leads to a severe decrease in said compound's physical properties and that a high degree of inventive skill is required in order to substitute said hydroxyl group for said halogen substituent of a particular compound without significantly adversely affecting the compound's physical properties, the following compounds were either prepared or acquired:

(BrCH₂CHBrCH₂O)₃P=O (hereinafter referred to as "A")

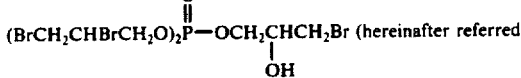

to as "B"),

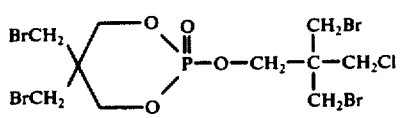

(hereinafter referred to as "C"), and

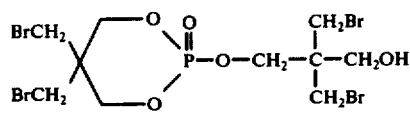

(hereinafter referred to as "D").

Compound A, tris(2,3-dibromopropyl)phosphate, is a well-known commercial flame retardant. For this example FireMaster[R] LV-T23P[R] brand tris(2,3-dibromopropyl)phosphate (Michigan Chemical Corporation, Chicago, Ill.) was employed.

Compound B, bis(3,2-dibromopropyl)-(3-bromo-2-hydroxypropyl)-phosphate, was prepared as follows: Into a three-neck 500 ml. flask equipped with a condenser, a stirrer, a thermometer, and a dropping funnel was placed 155 grams of bis(2,3-dibromopropyl)phosphoric acid (Acid No.: 100). Epibromohydrin (36.5 grams) was added at such a rate that an exothermic reaction was maintained at 50° C. After a one-hour addition, the flask was then heated an additional one hour at 60° C. The material was then washed with aqueous ammonia to a pH of 8 and washed with water. A thick orange liquid resulted (138 grams, 79 percent yield). After drying under reduced pressure, the product had the following analysis: Percent bromine calculated for $C_9H_{16}Br_5O_5P$: 63.2; Percent bromine found: 61.58.

Compound C, 2-(2',2'-bis(bromomethyl)-chloropropoxy)-5,5-bis(bromomethyl)-2-oxo-1,3,2-dioxophosphorinane, was prepared as follows: Dibromoneopentyl glycol (576 grams) was suspended in 600 grams of methylene chloride and cooled in ice to 10° C. Phosphorus trichloride (2.2 moles) was added over a six-minute period. An endothermic reaction developed with cooling to below 0° C. The ice bath was removed and the temperature was allowed to rise slowly (over a three-hour period) to 35° C. After cooling back to 10° C., 167 grams of chlorine were added with efficient cooling to keep the temperature below 35° C. The chlorine addition took 1.5 hours. The methylene chloride was removed under vacuum and 700 ml. of toluene were added. Magnesium oxide (2.5 grams) and 576 grams of dibromoneopentyl glycol were added and the mixture was heated to 90° C. The mixture was held at this temperture for 7.5 hours, cooled and filtered. The resulting white solid was reslurried with 500 ml. of cold toluene, filtered, and dried at 120° C. for 6 hours to yield 1024 grams (79 percent yield) of a white solid having a melting point of 150° to 152° C. Analysis for $C_{10}H_{16}Br_4ClO_4P$: Percent calculated: Br, 54.3; Cl, 6.04; Percent found: Br, 54.34; Cl, 7.03.

Compound D was prepared according to Example 1 above.

The thermal stability of compounds A, B, C, and D, above, was determined by the procedure set forth in Section 9-951, "Thermogravimetric Analyzer", of "Instruction Manual 990, Thermal Analyzer and Modules", E. I. Du Pont de Nemours and Co. (Inc.), Instrument Products Division, Wilmington, Del. 19898. The results of the thermogravimetric analyses (T.G.A) of the four compounds at several different weight losses are tabulated in Table V.

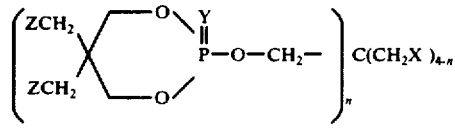

wherein each Z is independently selected from the group consisting of hydrogen and halogen; wherein

TABLE V

| Compound | Temperature at Which Weight Change Occurs, °C. | | | | Change in TGA, °C. | | Percent Change in TGA | |
|---|---|---|---|---|---|---|---|---|
| | A | B | C | D | B−A | D−C | (B−A)/A × 100% | (D−C)/C × 100% |
| 5% Weight Loss | 260 | 95 | 255 | 247 | −165 | −8 | −63 | −3 |
| 25% Weight Loss | 288 | 147 | 298 | 306 | −141 | +8 | −49 | +3 |
| 50% Weight Loss | 306 | 205 | 317 | 333 | −101 | +16 | −33 | +5 |

As with 2-(2',2'-bis(bromomethyl)-3-hydroxypropoxy)-5,5-bis-(bromomethyl)-2-oxo-1,3,2-dioxophosphorinane, other flame retardants within the scope of this invention, e.g., 2-(2',2'-bis(chloromethyl)-3'-hydroxypropoxy)-5,5-bis(chloromethyl)-2-oxo-1,3,2-dioxophosphorinane,2-(2',2'-bis(hydroxymethyl)-3'-bromopropoxy)-5,5-bis(bromomethyl)-2-oxo-1,3,2-dioxophosphorinane,2-(2',2'-bis(hydroxymethyl)-3'-chloropropoxy)-5,5-bis(chloromethyl)-2-oxo-1,3,2-dioxophosphorinane,2',2'-bis(hydroxymethyl)-1',3'-bis(5,5-bis(-bromomethyl)-2-oxo-1,3,2-dioxophosphorinane)propane, and 2',2'-bis(hydroxymethyl)-1'-3'-bis(5,5-bis(-chloromethyl)-2-oxo-1,3,2-dioxophosphorinane)propane, posses comparable hydrolytic and thermal stabilities when compared to their halogen or hydrogen, non-hydroxy substituted analogues.

Table V clearly demonstrates that the indiscriminate substitution of a hydroxyl group for a halogen atom of a compound will result in a dramatic decrease in the modified hydroxyl substituted compound's thermal stability. The only difference between the pair A and B and the pair C and D is the hydroxyl group. Therefore, one would expect the difference in thermal stability between the pair C and D to be of the same order as the substantial difference in thermal stability between the pair A and B. However, as shown in Table V, compound D's thermal stability is remarkably similar to the thermal stability of compound C and in some instances even better. Therefore, by use of a high degree of inventive skill, it was possible to effectuate a substitution of a hydroxyl group for a halogen atom and still maintain the basic physical properties of the nonhydroxyl-containing compound. The net result of this invention skill is that one is now hereby able to produce a reactive flame retardant capable of reactively being bound into a polymer chain and thereby reducing the migration and flame retardancy loss of the polymeric composition. This result has been long sought after and much desired in the art of flame retardants.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A compound of the formula:

each X is independently selected from the group consisting of hydrogen, halogen, and hydroxyl, provided that at least one X is hydroxy; wherein Y is selected from the group consisting of oxygen and sulfur; and wherein n is an integer from 1 to 3.

2. A compound according to claim 1 wherein each Z is independently selected from the group consisting of halogen; wherein each X is independently selected from the group consisting of halogen, and hydroxyl, provided that at least one X is hydroxyl; and wherein Y is oxygen.

3. A compound according to claim 2 wherein each Z is independently selected from the group consisting of chlorine and bromine; and wherein each X is independently selected from the group consisting of chlorine, bromine, and hydroxyl, provided that at least one X is hydroxyl.

4. A compound according to claim 3 wherein n is an integer from 1 to 2.

5. A compound according to claim 3 wherein n is 1.

6. A compound according to claim 1 selected from the group comprising 2-(2',2'-bis(bromomethyl)-3'-hydroxypropoxy)-5,5-bis(bromomethyl)-2-oxo-1,3,2-dioxophosphoriane; 2-(2',2'-bis(chloromethyl)-3'-hydroxypropoxy)-5,5-bis(chloromethyl)-2-oxo-1,3,2-dioxophosphoriane; 2-(2',2'-bis(hydroxymethyl)-3'-bromopropoxy)-5,5-bis(bromomethyl)-2-oxo-1,3,2-dioxophosphorinane; 2-(2',2'-bis(hydroxymethyl)-3'-chloropropoxy)-5,5-bis(chloromethyl) -2-oxo-1,3,2-dioxophosphorinane; 2',2'-bis(hydroxymethyl -1',3'-bis(5,5-bis(bromomethyl)-2-ox-1,3,2dioxophosphorinane) propane and 2',2'-bis(hydroxymethyl)-1',3'-bis(5,5-bis(chloromethyl)-2-oxo-1,3,2,-[dioxaphosphorinane]dioxophosphorinane) propane.

7. A polymeric composition comprising a polymer selected from the group consisting of polyurethane and polystyrene polymers and a flame retarding amount of a compound according to claim 1.

8. A polymeric composition according to claim 7 wherein each Z is independently selected from the group consisting of chlorine and bromine; wherein each X is independently selected from the group consisting of chlorine, bromine, and hydroxyl, provided that at least one X is hydroxyl; and wherein Y is oxygen.

9. A polymeric composition according to claim 8 wherein n is an integer from 1 to 2.

10. A polymeric composition according to claim 7 wherein the compound is selected from the group comprising 2-(2',2'-bis(bromomethyl)-3'-hydroxypropoxy)-

5,5-bis(bromomethyl)-2-oxo-1,3,2-dioxophosphorinane; 2-(2',2'-bis(chloromethyl)-3'-hydroxypropoxy)-5,5-bis(chloromethyl)-2-oxo-1,3,2-dioxophosphorinane; 2-(2',2'-bis(hydroxymethyl)-3'-bromopropoxy)-5,5-bis(bromomethyl)-2-oxo-1,3,2,-dioxophosphorinane; 2-(2',2'-bis(hydroxymethyl)-3'-chloropropoxy)-5,5-bis(chloromethyl)-2-oxo-1,3,2-dioxophosphorinane; 2',2'-bis(hydroxymethyl-1',3'-bis(5,5-bis(chloromethyl)-2-oxo-1,3,2-dioxophosphorinane) propane.

11. A polymeric composition comprising a polystyrene polymer and a flame retardant amount of a compound of the formula

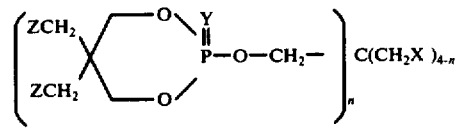

wherein each Z in independently selected from the group consisting of hydrogen, chlorine and bromine; wherein each X is independently selected from the group consisting of hydrogen, chlorine, bromine, and hydroxyl, provided that at least one X is hydroxyl; wherein Y is selected from the group consisting of oxygen and sulfur; and wherein $n$ is an integer from 1 to 3.

12. A compound of the formula:

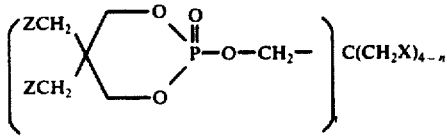

wherein each Z is independently selected from the group consisting of hydrogen and halogen; wherein each X is independently selected from the group consisting of hydrogen, halogen, and hydroxyl, provided that at least one X is hydroxyl; and wherein $n$ is an integer from 1 to 3.

13. A polymeric composition comprising a polymer selected from the group consisting of polyurethane and polystyrene polymers and a flame retarding amount of a compound according to claim 12.

* * * * *